(12) United States Patent
Cervi (10) Patent No.: US 6,875,183 B2
(45) Date of Patent: Apr. 5, 2005

(54) BIOPSY NEEDLE

(76) Inventor: Paul Laurence Cervi, 23 Holmwood Avenue, Shenfield, Essex CM15 8QS (GB)

( * ) Notice: Subject to any disclaimer, the term of this patent is extended or adjusted under 35 U.S.C. 154(b) by 197 days.

(21) Appl. No.: 09/955,790

(22) Filed: Sep. 19, 2001

(65) Prior Publication Data

US 2002/0042581 A1 Apr. 11, 2002

Related U.S. Application Data

(63) Continuation-in-part of application No. PCT/GB00/01003, filed on Mar. 17, 2000.

(51) Int. Cl.[7] .............................. A61B 5/00; B65D 81/00
(52) U.S. Cl. ..................................................... 600/567
(58) Field of Search ................................ 600/567, 568; 606/172, 180

(56) References Cited

U.S. PATENT DOCUMENTS

| | | | |
|---|---|---|---|
| 4,543,966 A | 10/1985 | Islam et al. | |
| 4,696,308 A | 9/1987 | Meller et al. | |
| 4,798,213 A | 1/1989 | Doppelt | |
| 5,133,359 A | * 7/1992 | Kedem | ........................ 600/567 |
| 5,357,974 A | * 10/1994 | Baldridge | .................... 600/567 |
| 5,556,399 A | 9/1996 | Huebner | |
| 5,595,186 A | 1/1997 | Rubinstein et al. | |
| 6,063,037 A | * 5/2000 | Mittermeier et al. | ......... 600/567 |
| 6,312,394 B1 | * 11/2001 | Fleming, III | ................. 600/567 |

FOREIGN PATENT DOCUMENTS

GB     2 164 277     3/1986

OTHER PUBLICATIONS

International Search Report; PCT/GB00/01003; Jun. 28, 2000; S. Hansen.

* cited by examiner

Primary Examiner—Max F. Hindenburg
Assistant Examiner—Brian Szmal
(74) Attorney, Agent, or Firm—Fish & Richardson, P.C.

(57) ABSTRACT

A biopsy needle for sampling bone marrow tissue, comprising a handle, and tissue sampling means comprising a sampling tube with a bore therein to receive a tissue sample, the outer surface of the sampling tube having an abrading formation extending in an axial direction along the tube, for abrading the sampled tissue, to permit the cannula tip to be laterally displaced whilst the tube is inserted into the bone marrow tissue. A biopsy needle for sampling bone marrow tissue, comprising a handle, tissue sampling means comprising a sampling tube with a bore therein to receive a tissue sample, and coupling means, separable from the needle, for coupling the needle to a rotary motor drive, whereby the needle is adaptable to both manual insertion and motor-assisted insertion.

27 Claims, 9 Drawing Sheets

BIOPSY NEEDLE

This application is a continuation-in-part (and claims the benefit of priority under 35 USC 120) of International application serial no. PCT/GB00/01003, filed Mar. 17, 2000. The disclosure of the prior application is considered part of (and is incorporated by reference in) the disclosure of this application.

This invention relates to apparatus and methods for sampling substances such as tissue, for example bone marrow tissue. More particularly it relates to improved bone biopsy needles and their use.

Tissue sampling is a common and important investigation in medical practice. Bone marrow is frequently retrieved for subsequent pathological study. Usually it is taken from the pelvic bone at the posterior superior iliac spine or iliac crest. Such a site is ideally suited to bone marrow sampling, as in adults there is often 3 to 5 centimeters of depth of cancellous bone (containing bone marrow) sandwiched between two 0.5 cm thick dense cortical walls of bone on the bone surfaces.

A useful review of bone marrow biopsy needles can be found of Chapter 3 of the "Manual of Bone Marrow Examination" by Anwarul Islam (Harwood Academic Pittsburg, 1998).

An early design, reusable needle (U.S. Pat. No. 4,262,676) called a "Jamshidi" after is inventor, is still in use today. It comprises a hollow metal tube or cannula to core out a cylindrical section of bone marrow, and a T-shaped handle. The cannula has a lumen which accommodates a stylet for initial insertion; the stylet being removed during the procedure to allow the harvesting of the bone marrow biopsy sample. The end of the stylet may be cut at an angle with the leading edge sufficiently sharp to pierce tissue and bone. Using a series of manoeuvres the operator detaches the biopsy specimen and withdraws it. The main problem with this design is that it is necessary, at the point of needle withdrawal, to forcibly tilt and rotate the needle many times in order to loosen the biopsy sample at the tip of the cannula This may cause distress both to the patient and operator. Sometimes the cannula bends, such is the force that is needed. Often it is necessary to make two or three passes to get one good sample.

Living bone marrow is a very complicated structure in engineering terms. It is composed of a semi rigid elastic lattice-work of trabecular bone composed of collagen, cartilage, calcium and hydroxyapetite, and the intervening space (80%) is occupied by the cellular constituents and fat—a very good lubricant. This means that sample retrieval is hampered by the double problem trying to extract tissue from a rigid structure with a lubricated cannula.

In the standard bone marrow procurement protocol, the patient is prepared with a suitable local anaesthetic at the appropriate marrow retrieval site. Then a bone marrow biopsy needle is inserted, with the stylet in place within the outer cannula, and the needle pushed through the outer layers of flesh until the bone is felt at the tip. The needle and stylet are then pushed approximately 4–5 millimeters further until the needle appears to be solidly within the outer cortical bone. The stylet is then removed from the needle, which opens up the core to the now-surrounding marrow tissue, and the needle is usually advanced another 1 to 4 centimeters with a twisting motion.

The cannula may be angled and provided with a sharpened edge to cut and core the tissue easily. By advancing the needle with a slight twisting motion, usually with no more than quarter or half turns, an appropriate sample is cored from the marrow tissue and enters the inner passage of the marrow needle.

It is at this point that the needle may be inadvertently inserted through the cortical bone of the deep surface of the bone and may possibly damage internal organ structures. It is a fairly common occurrence that the biopsy cannula penetrates the internal surface of the iliac bone, potentially damaging the internal organs of the pelvis (although, fortunately, it is rare that patients come to harm when this occurs). Difficulties in gauging the depth of the biopsy can be a problem particularly when the patient is overweight. There may be 5–10 cm of subcutaneous fatty tissue to penetrate before the bone surface is reached. A further difficulty arises because fatty tissue is variably compressible from patient to patient.

Once a sample has been cored, the marrow biopsy sample is ready to be removed from the patient, and the marrow biopsy sample must therefore be retained within the cannula and detached from the bone. If the biopsy becomes dislodged from the needle, and falls out of the cannula, the sample is irretrievably lost. The procedure must then be repeated from the beginning.

In order to retain the sample within the needle, the operator must dislodge the tip of the sample from the main section of the bone. One technique is for the operator to attempt to withdraw the cannula slightly, then tilt or rotate it and then advance the cannula again but this commonly fails and frequently causes distress to the patient. Alternatively the operator may apply suction during the removal of the cannula, but this also frequently fails.

Various modified needles (U.S. Pat. No. 3,605,721, Hallac; Islam; U.S. Pat. No. 5,074,311, Hasson; U.S. Pat. No. 5,634,473, Goldenberg) address this difficulty but all suffer from a number of disadvantages. Typically these designs involve complicated snaring, cutting or bending devices integrated into the tip of the biopsy needle, but none of these has become popular—probably because of the complicated mechanics and difficulties in manufacture and maintenance. With some there is a high failure rate, and often the biopsy sample is damaged or its size is compromised by, the necessary incorporation of devices within the cannula lumen to grip the sample at its tip. The best known successor to the Jamshidi is the Islam needle, in which the cannula is modified by having a sharp inner collar near the tip which grasps the biopsy sample at the point of needle withdrawal. A newer disposable needle from Medical Device Technologies Inc., which involves the insertion of a second cannula within the primary cannula, is also successful at gripping the sample. However both these devices result in narrow, and occasionally damaged biopsy samples.

GB 2,164,277 describes a bone drill with saw teeth at the tip and a groove between each consecutive pair of teeth extending part-way along the outer surface of the drill's shank to permit the escape of bone dust. U.S. Pat. No. 4,798,213 describes bone biopsy apparatus having similar grooves and an inner retaining sheath for the biopsy sample consistency of two separable longitudinal paths which separate when the inner retaining sheath is removed from an outer retaining sheath. U.S. Pat. No. 4,543,966 describes a biopsy needle with flutes at the tip and an internal shoulder to assist sample retention. U.S. Pat. No. 4,696,308 describes a core sampling apparatus comprising a drill element, an adapter, and a chuck for an associated driving tool. U.S. Pat. No. 5,595,186 describes a bone marrow biopsy needle comprising an inner tube slidable through the lumen of an outer tube, the inner tube including a pair of pincers at its distal end for grasping a biopsy core. U.S. Pat. No. 5,556, 399 describes a bone-harvesting drill apparatus for harvesting bone for transplantation; the harvested bone fragments are not suitable as biopsy specimens.

Sometimes when the bone marrow is very soft, as in patients with osteoporosis, almost all attempts to procure a biopsy sample will be unsuccessful because the bone structure is so fragile. Conversely sometimes the bone structure is very fibrotic/sclerotic and it is very difficult to insert the cannula and subsequently to remove the core biopsy. This is because the bone marrow itself is reinforced by the surrounding tissue, frequently resulting in failure of the procedure.

As can be seen, the current procedures and instruments are flawed in a number of respects. There therefore exists a need for an improved bone marrow biopsy needle. Preferably this should ensure reliable retrieval of the sample without compromising the size of the sample, and preferably, should reduce the risk of accidentally harming internal organs during the biopsy procedure.

In accordance with the present invention there is therefore provided a biopsy needle for sampling bone marrow tissue, comprising; a handle; and tissue sampling means comprising a sampling tube with a bore therein to receive a tissue sample, the outer surface of the sampling tube having an abrading formation extending in an axial direction along the tube; characterized in that the abrading formation comprises a slot cut into the wall of the sampling tube with at least one sharpened edge where the slot meets the outer wall of the sampling tube to abrade the sampled tissue, to permit the tip of the sampling tube to be laterally displaced whilst the tube is inserted into the bone marrow tissue.

The abrading formation acts somewhat like a saw in that it allows the operator, by manipulation of the handle, to cut or abrade away unwanted material to create a small cavity in the bone in the vicinity of the sampling tube tip. This allows the sampling tube tip to be moved laterally, abrading the surrounding tissue, whilst the biopsy needle is inserted in the marrow tissue. When the biopsy needle is inserted into the marrow, a core sample is obtained which is attached at its inner most end to the bulk of the surrounding tissue. Moving the tip of the sampling tube laterally assists in breaking the attachment so that the sample can be readily withdrawn Preferably the sampling tip or cannula extends through the handle of the biopsy needle to simplify manufacture and use. Such a biopsy needle may readily be made reusable and simple to operate.

According to another aspect of the invention there is provided a method of sampling a substance using a needle, the needle having a handle and sampling means comprising a sampling tip with a bore therein to receive a sample of the substance, the sampling tip having a formation on its outer surface for abrading the substance, the method comprising the steps of:
i) inserting the sampling tip into the substance to be sampled to collect a sample within its bore;
ii) moving the sampling tip such that the substance is abraded to allow the sampling tip to be displaced sufficiently to weaken the connection between the sample and the bulk of the substance; and
iii) withdraw the sampling tip with the sample therein.

Thus the sample can be effectively detached without the need to compromise the sample's diameter. The biopsy needle requires little manipulation to detach the sample, thus decreasing patient pain and anxiety, and makes it much easier to reliably obtain a biopsy sample. This saves time, effort, money and patient distress.

In one embodiment the sampling tip is moved by gently tilting and rotating the needle, preferably a number of times. Thus the needle may be tilted by 10° to 15° such that the abrading formation is pressed against the surrounding bone, and then gently rotated backwards and forwards by, say, 45°, until the needle feels loose within the bone.

Utilising an abrading formation comprising an abrading edge cut into the wall of the sampling tube facilitates manufacture of the needle, reducing its price. For ease of needle manipulation, it is desirable that the abrading formation extends along the outer surface of the sampling tube for at least one or two centimeters. In one embodiment the edge is ridged to facilitate abrasion using a sawing action.

In one embodiment the slot extends through the full thickness of the cannula wall. This allows ingress of fatty marrow tissue debris into the cannula as this is moved to abrade the surrounding tissue. It has been found that this helps to hold the biopsy specimen within the cannula.

In another embodiment, the abrading formation comprises a plurality of linear indentations. This embodiment is preferred to one where the abrading formation comprises a slot extending through the fill thickness of the cannula wall for some applications, as the sample is enclosed at the sides and because there is less weakening of the cannula The sample is thus better protected and there is also less risk of damage when expressing the sample. This is useful when, for example, sampling the soft bone of an elderly patient, when a reduced expression force is desired. This can be traded against a slight reduction in grip of the sample within the cannula, according to the needs of an application. The indentations can be spaced circumferentially around the cannula, for example, to reduce the need for an operator to be aware of the orientation of the needle with respect to the abrading formation.

Advantageously a sample detacher is provided at the tip of the cannula to assist in detaching the sample from adjoining tissue. In a preferred embodiment this comprises, a short, longitudinal slot or recess substantially opposite a longer recess of the abrading formation. This short slot or recess, which is advantageously provided with a sharpened edge, effectively cuts at the base of the biopsy sample as the needle is being manipulated to rub the abrading formation against the interior surface of the hole in the bone made by the cannula to assist in detaching the sample from adjoining tissue. Thus the cutting action is provided at the same time as the cannula tip is displaced. The slot or recess may be readily formed as a cut at least 1 or 2 mm in length, in the cannula tip wall. The presence of the slot or recess tends to snare the end of the biopsy sample at the cannula tip and thus also helps retain the sample in the cannula.

In other embodiments, several short recesses or cuts may be provided at the tip of the cannula, for example, two to four circumferentially spaced transmural cuts. This assists ingress of sampled material and bony debris, improving abrasion and increasing adhesion of the sample to the needle at the tip. This is particularly preferable when the abrading formation does not extend through the full thickness of the cannula wall, since in this arrangement the sample is effectively gripped mainly at the tip.

Advantageously a biopsy needle can also be coupled to a motor drive. According to another aspect of the invention there is therefore provided a biopsy needle for sampling bone marrow tissue, comprising: tissue sampling means comprising a sampling tube with a bore therein to receive a tissue sample; a handle connected to the tissue sampling means for manual insertion of the biopsy needle; and coupling means, detachably connected to the tissue sampling means, for coupling the needle to a rotary motor drive; whereby the needle is adapted for both manual insertion and motor-assisted insertion.

Occasionally unexpected resistance to the insertion of the bone marrow biopsy needle is encountered and therefore the needle is adaptable to both manual and motor assisted insertion. Preferably the motor drive coupling means is a detachable accessory so that it can be supplied separately, for use as and when required. A cordless electric screw driver provides a suitable motor drive. To facilitate the use of such a device in an aseptic surgical procedure there is preferably provided an insulating sterile or sterilizable, protective sheath, to substantially enclose the motor drive except for a drive shaft, and to allow operation of the motor drive whilst within the sheath.

According to a further aspect of the invention there is provided a coupling means for use with the biopsy needle, comprising a shaft adapted to be received by the sampling tube of the biopsy needle, a connecting portion for connecting the motor drive and a drive portion to engage with the handle.

Preferably the biopsy needle incorporates a guard or stop to inhibit over-insertion of the cannula into the tissue being sampled. This may comprise an enlargement of the circumference of the needle at the requisite distance, typically between 2 and 3 cm, from the cannula tip. The stop should be small enough to be able to penetrate the skin and subcutaneous tissue, but should be sufficiently wide to prevent its further insertion into the bone, thus limiting the depth to which the cannula penetrates. To assist in penetration of the skin, a small skin incision may be made; this also facilitates healing with less scar formation.

The stop may be readily provided by extending the biopsy needle handle along the shaft of the needle to the required distance. For simplicity of manufacture the stop is preferably moulded, bonded or otherwise formed as one part with the handle (which is typically a plastic moulding). In another embodiment the position of the stop on the cannula is adjustable.

These and other aspects of the invention will now be further described, by way of example only, with reference to the accompanying figures in which.

Figures 1A, 1B, 1C, 1D:
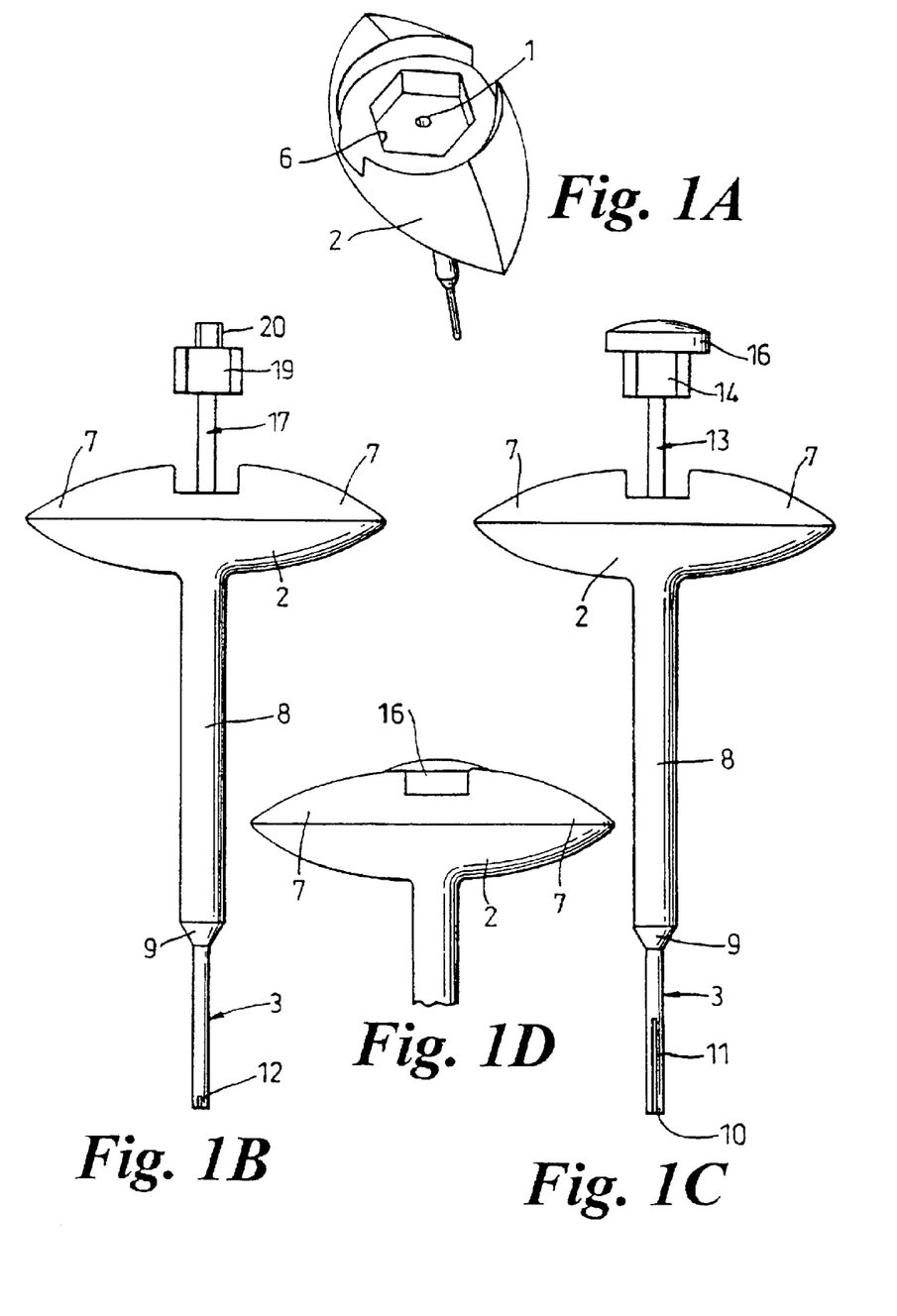
FIGS. 1A to 1D, show, respectively, a perspective view from the top of an embodiment of a biopsy needle according to the present invention; a side view of the biopsy needle with a partially inserted motor drive coupling; a side view of the needle with a partially inserted stylet; and a partial side view of the needle with the stylet fully inserted.
Figure 2A:
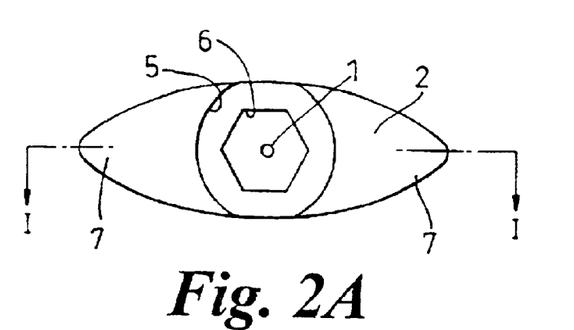
FIGS. 2A to 2C show, respectively, a top view of a biopsy needle; a side view of a biopsy needle; and a cross-section through the needle of FIG. 2A along the line I—I.
Figure 2B:
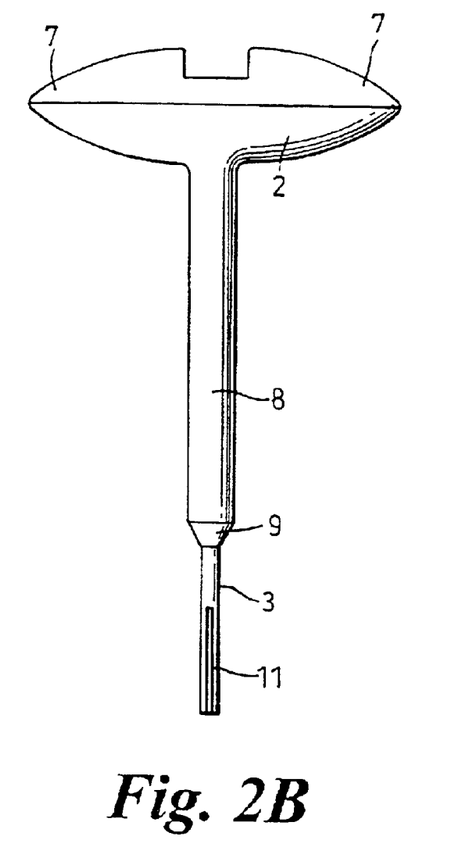
Figure 2C:
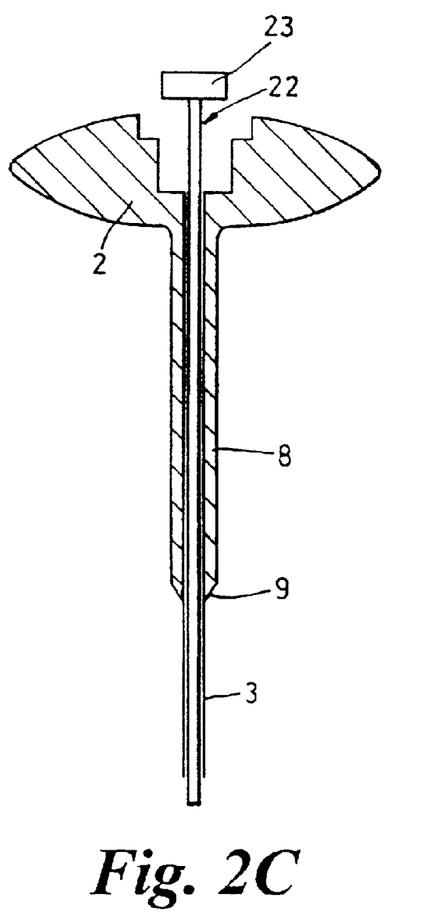
Figure 3A:
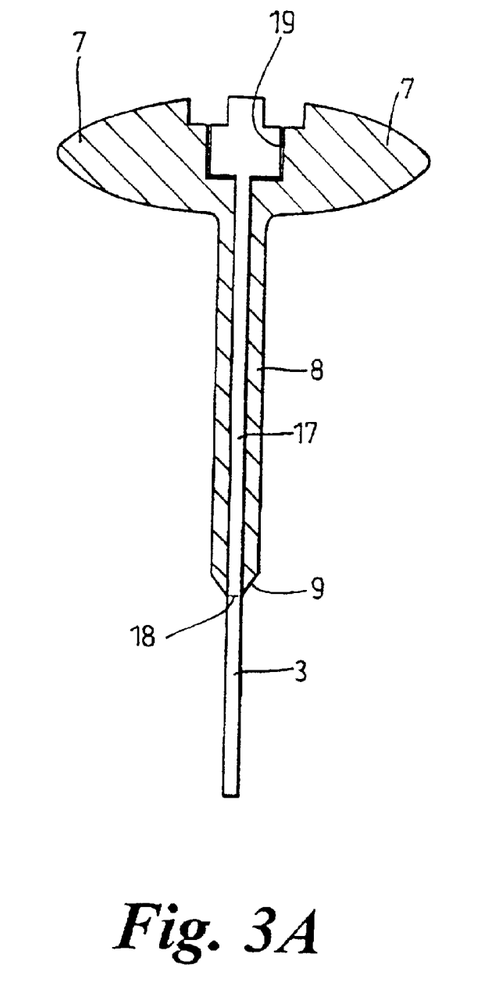
FIGS. 3A and 3B show, cross-sections through a biopsy needle with respectively, a motor drive coupling, and with a stylet.
Figure 3B:
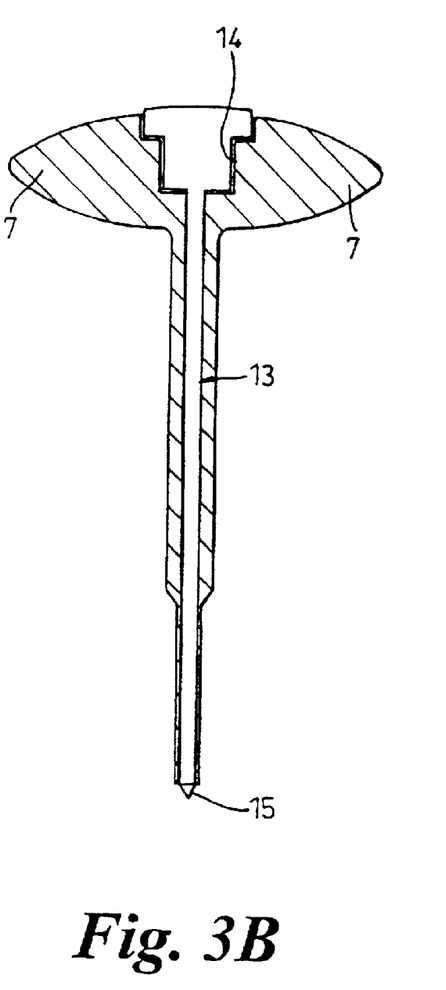
Figure 4A:
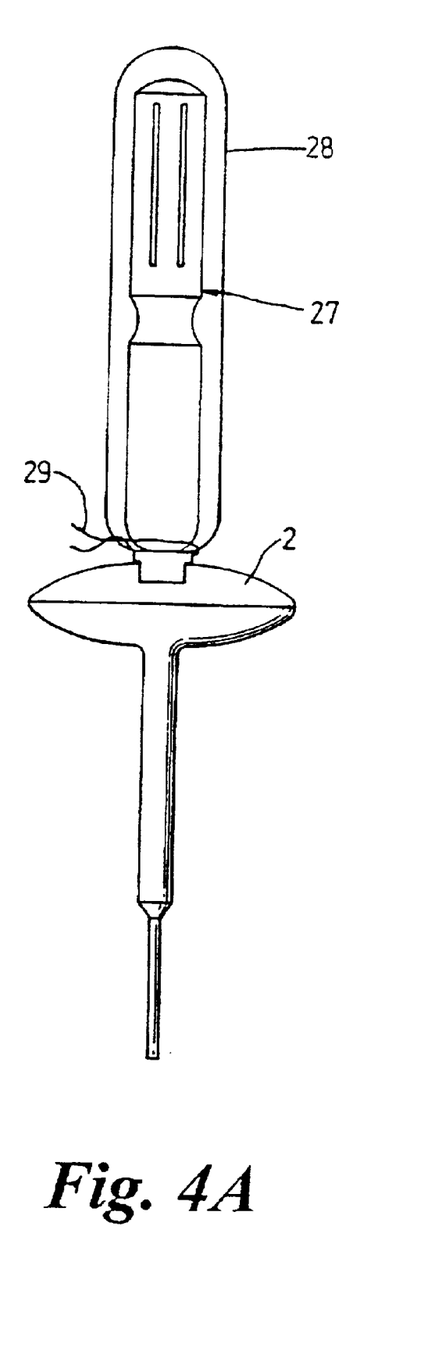
FIGS. 4A and 4B show, respectively, a side view and a sectional view of a biopsy needle with a motor drive attached.
Figure 4B:
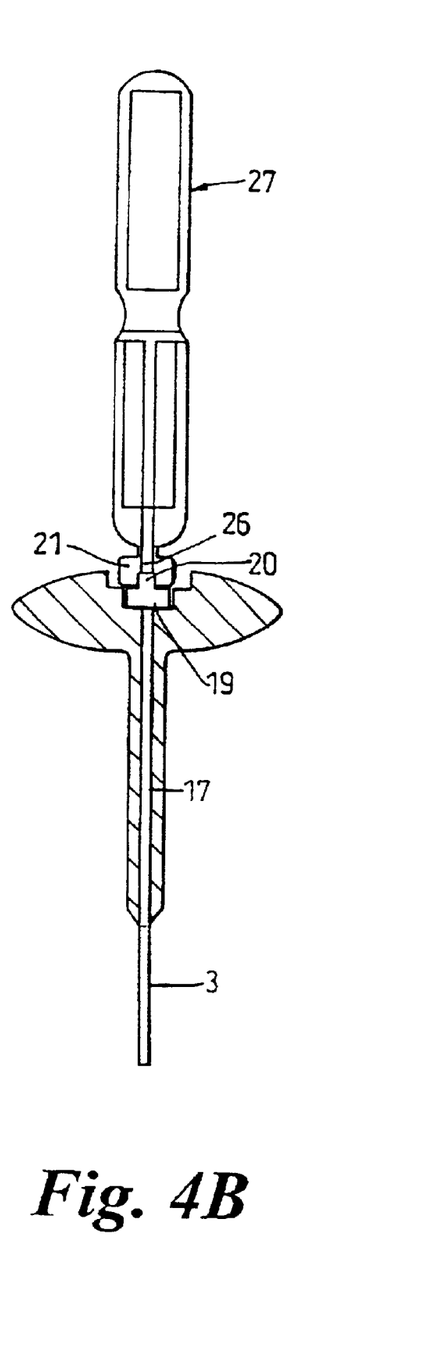
Figures 8A, 8B, 8C:
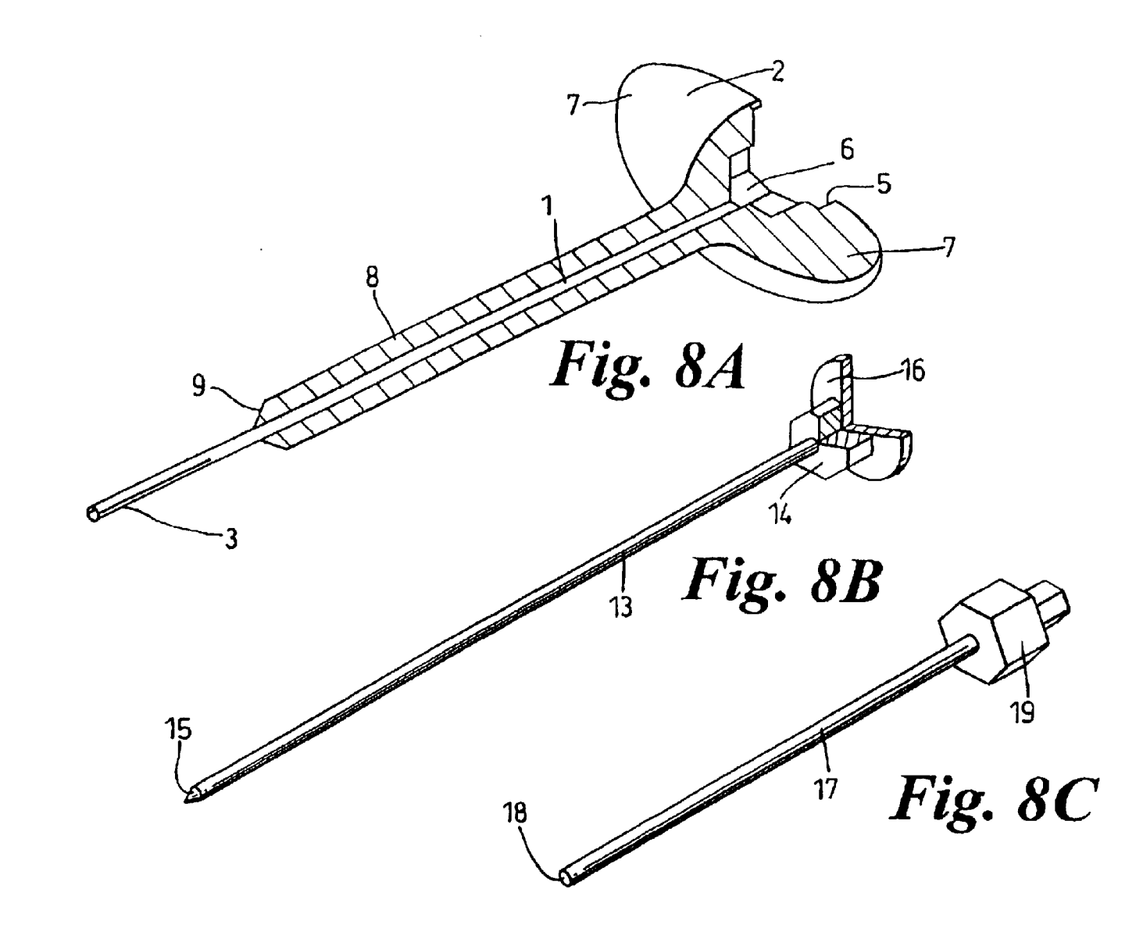
FIGS. 8A to 8C show, respectively, a cut-away view of a biopsy needle; a cutaway view of a stylet; and a perspective view of a motor drive coupling.

Referring to FIGS. 1, 2, and 8, these show a biopsy needle in accordance with one embodiment of the invention. The biopsy needle has a handle 2 at one end and a tissue sampling tube or cannula 3 at the other end. The handle has laterally extending wings 7 to assist in inserting the cannula into tissue, particularly bone marrow tissue, which is to be sampled. The cannula has a bore or lumen 1 to receive a sample of the tissue. This lumen preferably extends from the cannula tip to an opening in the handle, as shown in FIG. 1A. This allows a syringe to be attached to the biopsy needle so that suction can be applied to the lumen, if required, to assist in retaining a tissue sample in the needle.

The lower portion 8 of the handle extends over a part of the cannula to enlarge the diameter of the biopsy needle up to a point 9, which acts as a stop. This stop is positioned at distance from the tip of the cannula equal to the desired maximum length of bone marrow sample. The stop 9 abuts against the periosteum of the bone being sampled and prevents the cannula from being inserted more than the desired maximum length.

In adults the desired maximum length is usually no more than 3 to 3.5 cm; in a paediatric needle the maximum desired length is typically no more than 2 cm. The stop position may, if desired, be made adjustable by providing a screw mechanism on the handle.

The sampling tube 3 need extend only a short distance into handle extension portion 8 and the bore in the sample tube need only be long enough to hold the desired maximum length of bone marrow sample. However, it is preferable that the sampling tube, and the bore therein, extends through the length of the handle (as shown in the figures) as is conventional with a cannula.

Conveniently the handle is formed in two moulded parts which are fitted around the cannula and secured to the cannula by friction, bonding or keying means. Alternatively the handle may be injection moulded around the cannula, with the cannula in place, in a single stage manufacturing process.

The sampling end of the cannula is provided with an abrading or sawing formation 11 and a cutting formation 12. In a preferred embodiment these are both longitudinal slots extending from the cannula tip and cut through the wall of the cannula. These are shown in close up in FIG. 5C. Preferably the operator can determine the orientation of formation or slot 11 whilst the biopsy needle is in use, for example by means of a spot of paint on the handle.

Figures 5A, 5B, 5C:
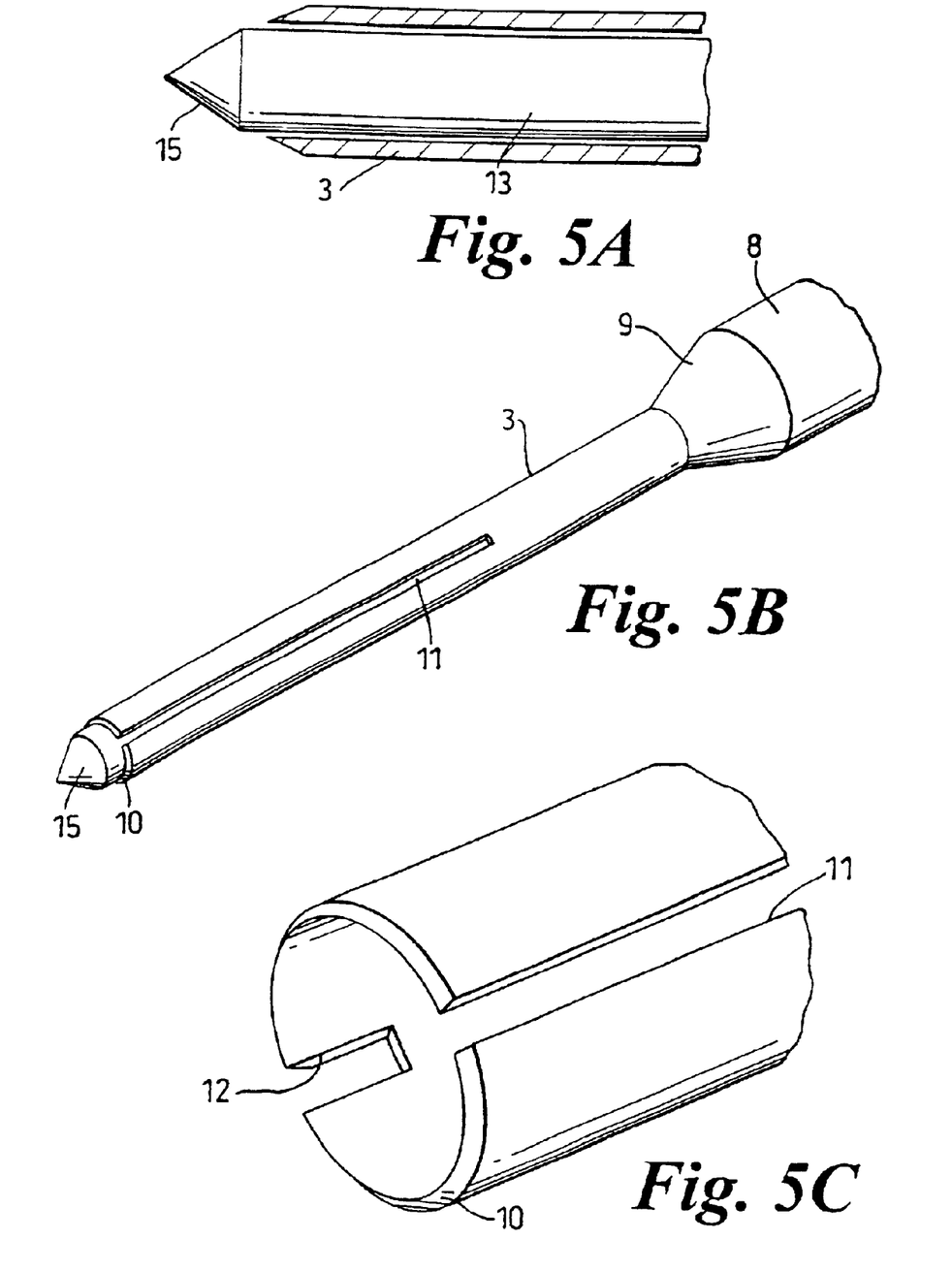
FIGS. 5A to 5H show, respectively, a longitudinal section through a first embodiment of a cannula tip with a stylet inserted; a perspective view of a first embodiment of a cannula with a stylet inserted; a perspective view of a first embodiment of a cannula tip; a longitudinal section through a second embodiment of a cannula tip; a side view of the second embodiment of the cannula tip; a transverse section through the cannula tip of FIG. 5D along line I—I; a perspective view of the second embodiment of the cannula tip; and a transverse section through the cannula tip of FIG. 5D along line II—II.
Figure 5D:
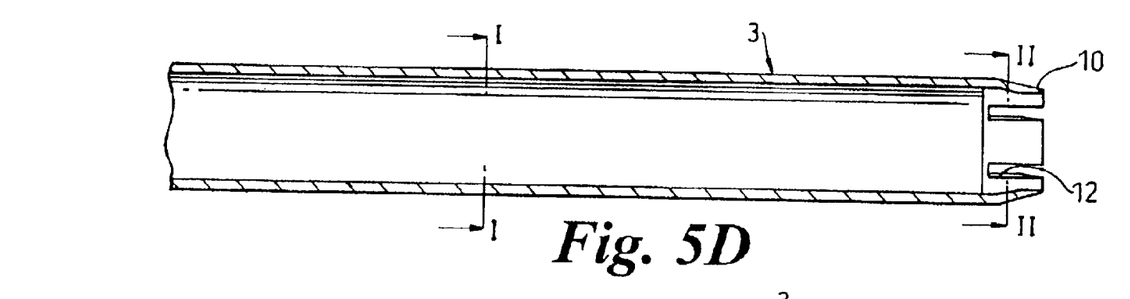
Figure 5E:
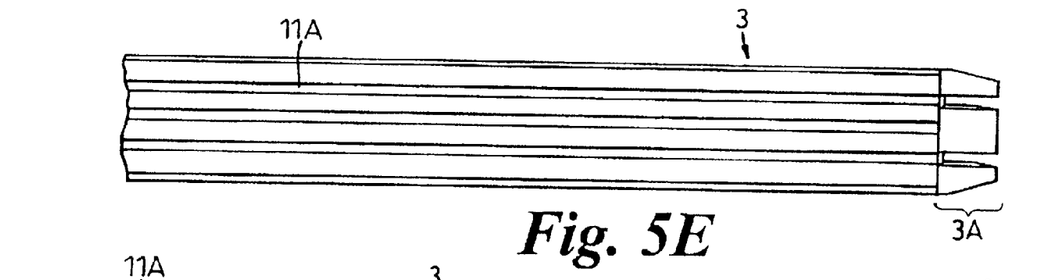
Figure 5F:
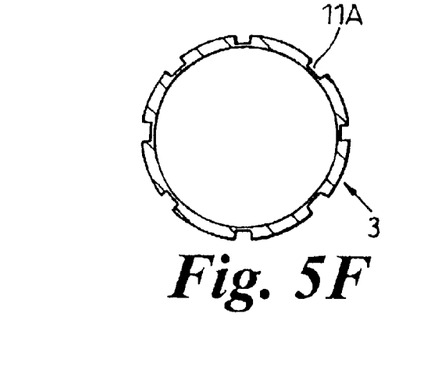
Figures 5G, 5H:
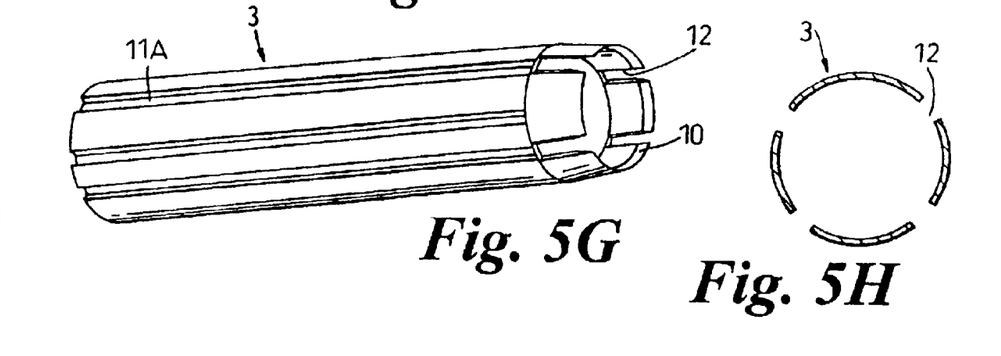

Referring to FIG. 5C, the cannula has a sharpened, bevelled tip 10 to assist in inserting biopsy needle and cutting the tissue specimen. In a preferred embodiment, the slot 11 is between 1.5 and 3 cm long and has a width of between 0.25 mm and 1 mm, and preferably of approximately 0.5 mm. Preferably the slot runs perpendicularly from the cannula tip in an axial direction and at least one end of the slot, where it meets the outer wall of the cannula, has a sharpened edge for abrading the bone marrow. The abrading function of slot 11 may be performed by a series of edges or by another abrading surface or shape. In other arrangements the cannula tip may be substantially semi-circular or U-shaped.

The (or, in alternative embodiments, each) short slot 12 has a length of approximately 1 to 2 mm and a similar width to that of the long slot, that is about 0.5 mm. Again at least one and preferably both outer edges of this slot are sharpened. Preferably the short slot 12 is positioned opposite end long slot 11 so that when slot 11 is being used to abrade the bone marrow, slot 12 is cutting at the base of the biopsy specimen.

FIGS. 5D to 5H show a second embodiment of a cannula which, rather than the single slot of FIGS. 5B and 5C, comprises a plurality of linear, longitudinal indentations 11A, and ridges therebetween to abrade the bone marrow. It can be seen from FIG. 5F that the indentations do not extend through the full thickness of the cannula wall. This embodiment also has a plurality of short slots 12 disposed at the cannula tip. As illustrated, slots 12 extend substantially the length of a final tapered portion 3A of the cannula.

In some embodiments the cannula does not narrow significantly towards its tip, and because there is no internal device for grasping the biopsy sample, the sample can occupy substantially the full internal dimensions of the cannula. This maximises the specimen size for a given dimension of needle and thus allows smaller needle to be used than would otherwise be the case, reducing the pain experienced by the patient In other embodiments there is slight (about 5–10%) narrowing. A slight narrowing of the cannula tip helps reduce the expression force needed to dislodge the sample and there is therefore potentially less damage to the sample at this time, whilst providing only slightly narrower samples.

The biopsy needle is provided with a removable stylet 13, as shown in FIG. 3B, FIGS. 5A and 5B, FIGS. 6A and 6F and FIG. 8B. (FIG. 1D shows the head 16 of the stylet when inserted in handle 2). The stylet has a shaft which fits within the bore of the cannula and a head 16 which sits in a recess 6 in the handle with the top of the head flush with the handle surface. When the stylet is so inserted a sharpened tip 15 of the stylet projects slightly from the sharpened tip of the cannula. The stylet obstructs the sampling tube bore prior to insertion of the biopsy needle into the sampled tissue and assists in the penetration of the hardened outer cortical bone.

The broad top of head 16 assists the operator in applying axial force on the stylet as the needle is being inserted. The head 16 is preferably sized to frictionally engage with the recess in the handle; it has a hexagonal base 14 which engages with a corresponding hexagonal aperture in recess 6. This prevents the stylet from twisting as the needle is inserted, which is useful when the stylet tip 15 has a cutting or drilling edge rather than a smooth conical shape.

Figure 6A:
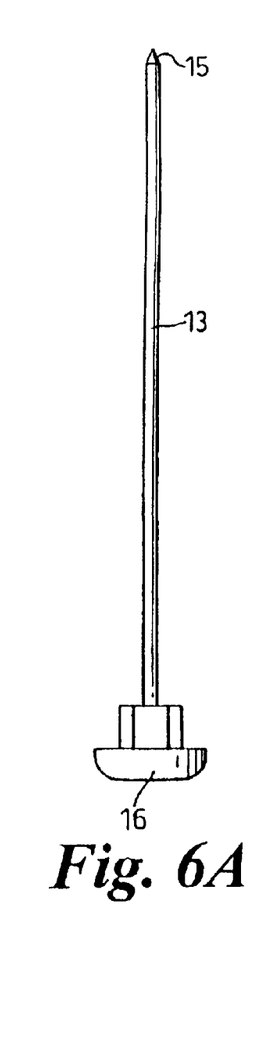
FIGS. 6A to 6F show various perspective views of, respectively, a stylet; a pushrod; a motor drive coupling; a motor drive coupling; a pushrod; and a stylet.
Figures 6B, 6C, 6D, 6E, 6F:
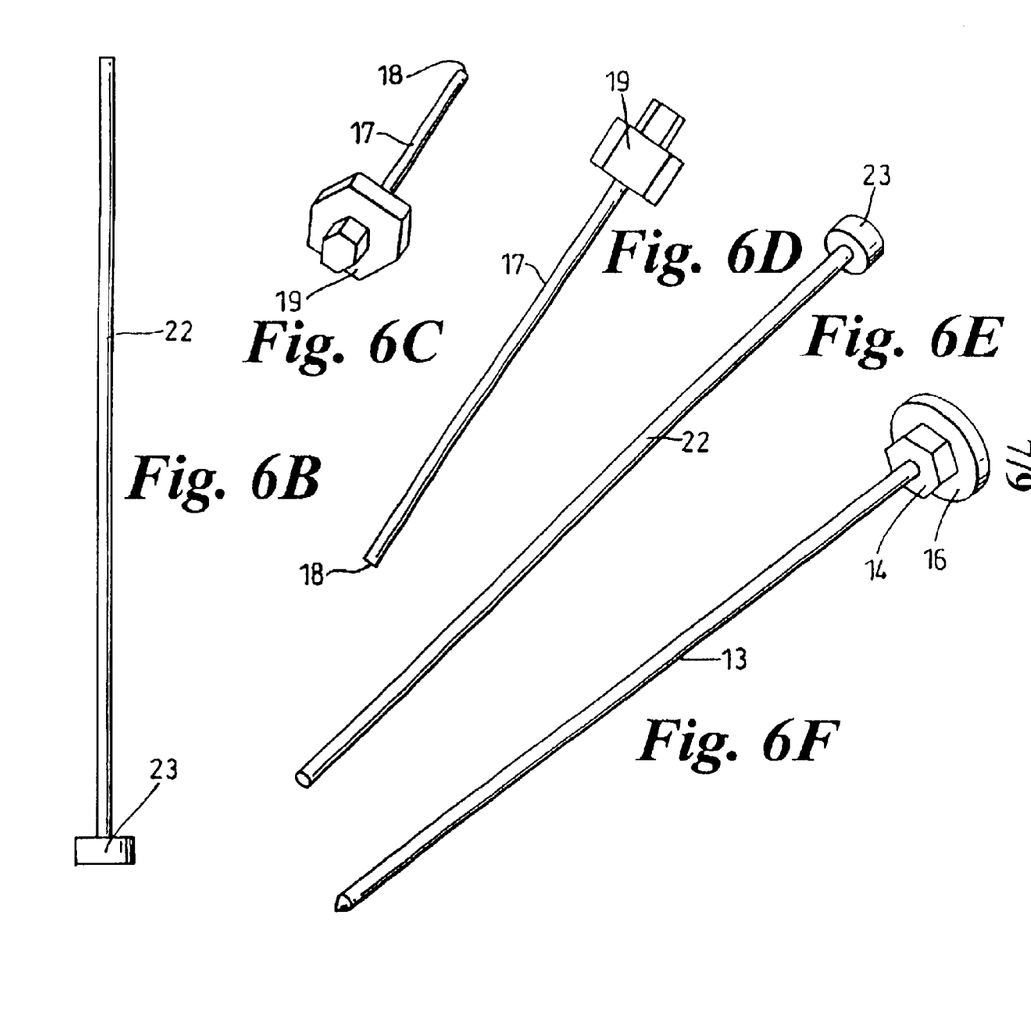

Also associated with the biopsy needle is a pushrod 22 with a head 23 (see FIGS. 2C, 6B and 6E). The pushrod has a shaft which fits slidingly within the cannula lumen, and is used to express the biopsy sample from the needle after the needle has been removed from the patient. Alternatively a thin push rod could be inserted into slot 11 from the side of the cannula, although this arrangement is not preferred as it tends to damage the sample.

Optionally the biopsy needle may be provided with a removable motor drive coupling 17, as shown in FIGS. 1B, 3A, 4A and 4B, 6C and 6D, 7D and 8C. This coupling comprises a shaft which fits within the cannula lumen, a drive portion 19 and a connecting portion 20 for connecting a motor drive. In the illustrated embodiment drive portion 19 is a hexagonal formation which seats in the same hexagonal aperture in recess 6 as the stylet. Using a common means for engaging both the stylet and the motor drive coupling with the handle simplifies the handle construction.

The length of the motor drive coupling shaft is chosen so that when the motor drive coupling is fully inserted into the biopsy needle the shaft does not obstruct the sample holding-cavity within the cannula. Preferably the length of the shaft is chosen so that its end 18 is located approximately at the same position as the stop 9, it thereby acting as a farther safeguard against excessive penetration of cannula 3 into the bone to be sampled.

The motor drive connecting portion 20 is chosen to suit the motor drive employed and, in the illustrated example, comprises a hexagonal stub. The motor drive 27 may be constructed or adapted specifically to suit its intended purpose, but conveniently a suitable motor drive can be provided by an electric screw driver. These are generally fully enclosed, battery driven (and hence free of external wiring), portable and capable of a high torque output. An output shaft of the motor drive has a chuck 26, advantageously with a guard 21, which holds stub 20 (shown in FIG. 4B, omitting some details).

The motor drive preferably has an insulated outer casing and is substantially enclosed within a transparent rubber or plastic sterile sheath 28, facilitating its use in a surgical procedure. In a preferred embodiment the sheath 28 is sized to fit around the motor drive and is fastened with draw strings 29 or other fastening means, about the drive shaft 26. A sheath made from thin plastic or rubber does not interfere with operation of the motor drive and readily allows operation of its controls.

In a preferred embodiment the motor drive rotates the whole biopsy needle, that is both the cannula and the handle.

FIG. 7 shows steps in the use of the biopsy needle. In FIG. 7A the cancellous bone 34, which contains bone marrow, lies between outer cortical bone 30 and deep periosteal surface 35, under sub-cutaneous tissue 32 and the patient's skin 31. It is preferable to make an initial incision through the anaesthetized patient's skin and sub-cutaneous tissue using a suitable knife or lancet 36.

Figure 7A:
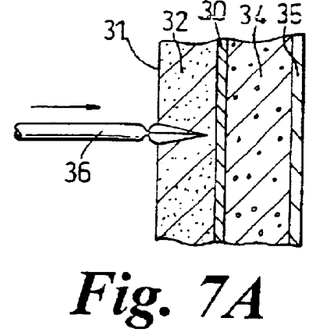
FIGS. 7A to 7H show steps in a method of using a biopsy needle.
Figure 7B:
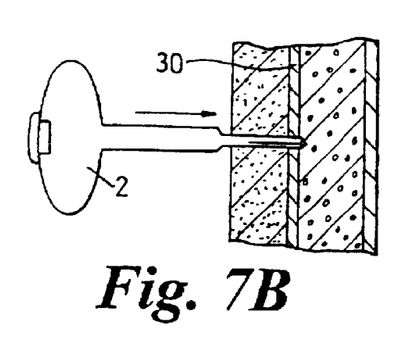
Figure 7C:
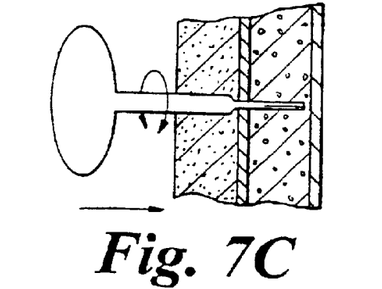
Figure 7D:
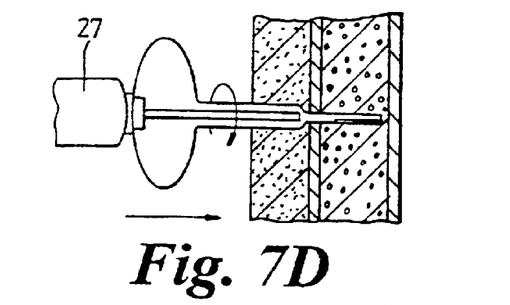

The operator then inserts the biopsy needle, with the stylet in position, through the skin and subcutaneous tissue until the cannula penetrates the outer cortical bone 30 (FIG. 7B). The stylet is then removed from the centre of the cannula (whilst retaining the cannula in position) and then the needle is advanced manually through the cancellous bone 34 by applying gentle inward force combined with a backwards and forwards rotational movement of the needle (FIG. 7C). In about 10% of cases it is difficult to manually core the bone and if substantial resistance is encountered, the motor drive can be attached as shown in FIG. 7D. In all cases, however, it is preferable to start coring the bone marrow manually.

The inward force is released once a core sample of the desired length has been obtained, normally when the stop has abutted against the outer cortical bone 30. It is then necessary to detach the end of the core sample from the surrounding bone so that the sample can be removed To do this the operator tilts the needle so that the abrading formation 11 is brought into abrading contact with the cancerous bone 34; typically around 10 to 15 degrees tilt is necessary.

Figure 7E:
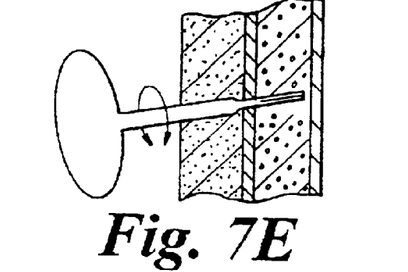
Figure 7F:
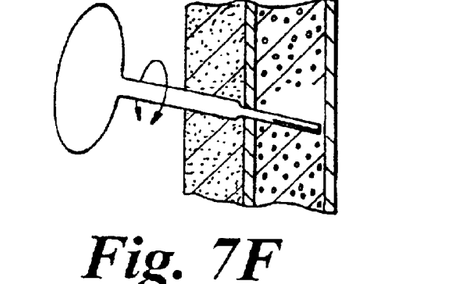

The needle is then gently rotated backwards and forwards to abrade the bone on one side of the inner surface of the hole created by the cannula. It is continued until the needle feels loose within the bone, as shown in FIG. 7E. If desired the biopsy needle can be rotated through 180° and the same procedure repeated to abrade the opposite side of the hole in the bone (FIG. 7F). Whilst the biopsy needle is tilted, at the same time at the bone is being abraded by formation 11, formation 12 is cutting away at the base of the sample to assist in detaching the sample from adjoining tissue.

Figure 7G:
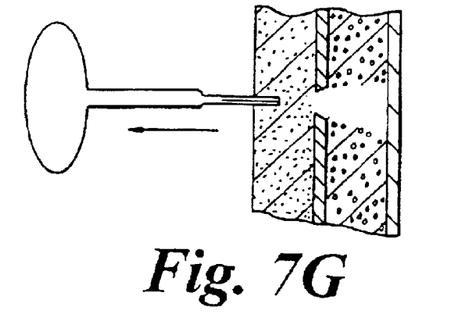
Figure 7H:
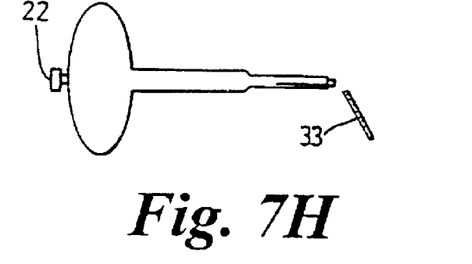

In most cases, the result of this procedure is that the sample is freed from its attachment to the surrounding bone, allowing the biopsy needle with the sample to be withdrawn as shown in FIG. 7G. The biopsy sample 33 can then be expressed from inside the cannula using pushrod 22, as shown in FIG. 7H.

The abrading motion shown in FIG. 7E and 7F creates a fluid filled space around the cannula and when the abrading formation 11 extends through the thickness of the cannula wall, marrow fluid and fatty tissue from the cavity enters the cannula and increases the adhesion of the marrow sample within the biopsy needle, increasing the likelihood of successfully retrieving a sample.

No doubt many variations of the invention will occur to the skilled person and it should be understood that the invention is not limited to the described embodiments. In particular, applications of the needle are not limited to sampling bone marrow tissue. For example, embodiments of the present invention are also useful for bone biopsy, and for the aspiration of fluid from the bone marrow cavity for diagnostic purposes, and for the retrieval of large volumes of fluid for the purpose of bone marrow transplants. Further, embodiments of a needle according to the present invention can also be used for obtaining a core sample of other solid matter, for example, wood, particularly where there is a need for minimal surface damage.

What is claimed is:

1. A biopsy needle instrument for sampling bone marrow tissue, said instrument comprising:
   a handle for inserting said needle into the bone marrow tissue; and
   said needle further comprising a single hollow tube, configured for both cutting and receiving a bone marrow tissue sample, coupled to said handle;
   said tube having (a) a tube bore defining a tissue-receiving space for the bone marrow tissue sample, (b) a substantially rigid tip, and (c) an outer wall configured to contact the bone marrow tissue, said outer wall being provided with an abrading formation comprising at least one slot cut into said outer wall, said slot having at least one sharp edge, said slot having a width of less than about 1 mm, said abrading formation extending in an axial direction along said tube to abrade the bone marrow tissue and thereby to allow said tip of said single hollow tube to be laterally displaced within the bone marrow tissue to facilitate retrieval of the bone marrow tissue sample.

2. A biopsy needle as claimed in claim 1, wherein two outer edges of said slot are defined by the intersection of said slot with said outer wall, and wherein both said outer edges are sharp.

3. A biopsy needle as claimed in claim 1, wherein said slot extends through said sampling tube between said outer wall and said bore.

4. A biopsy needle as claimed in claim 1, wherein said abrading formation comprises a plurality of said slots spaced circumferentially about said tube.

5. A biopsy needle as claimed in claim 4, wherein said slots of said abrading formation are spaced from said tip.

6. A biopsy needle as claimed in claim 1, wherein said slot extends, in an axial direction, at least 1 cm from said tip.

7. A biopsy needle as claimed in claim 1, wherein said tube further comprises a sample detacher at said tip to assist in detaching a base portion of said tissue sample from adjoining tissue.

8. A biopsy needle as claimed in claim 7, wherein said sample detacher comprises a sample detacher slot cut into a wall of said tip.

9. A biopsy needle as claimed in claim 8, wherein said sample detacher slot extends through said wall of said tip.

10. A biopsy needle as claimed in claim 8, wherein said sample detacher comprises a plurality of said sample detacher slots circumferentially about said tip.

11. A biopsy needle as claimed in claim 8, wherein said sample detacher slot has a length of between 1 mm and 2 mm.

12. A biopsy needle as claimed in claim 7, wherein at least a part of said sample detacher is disposed on said tube substantially opposite at least a part of said abrading formation.

13. A biopsy needle as claimed in claim 1 further comprising a stop to inhibit over-insertion of said tube into the bone marrow tissue being sampled.

14. A biopsy needle as claimed in claim 13, wherein at least a portion of said stop is integrally formed with at least a portion of said handle.

15. A biopsy needle as claimed in claim 1, wherein said tube bore extends through said handle.

16. A biopsy needle as claimed in claim 15, wherein said handle is adapted for connection of a suction device to said tube bore.

17. A biopsy needle as claimed in claim 15 further comprising a coupling for coupling said biopsy needle to a motor drive for rotation of said tube.

18. A biopsy needle as claimed in claim 17, wherein said coupling is separable from said needle and comprises a shaft adapted to be received by said tube, a connecting portion for connecting said motor drive, and a drive portion to engage with said handle.

19. A biopsy needle as claimed in claim 1 wherein said tube has a sharpened, beveled tip.

20. A biopsy needle for sampling bone marrow tissue, comprising:
    a tissue sampling member comprising a sampling tube with a bore therein to receive a tissue sample;
    a handle connected to said tissue sampling member for manual insertion of the biopsy needle; and
    a coupling member, detachably connected to said tissue sampling member, for coupling said needle to a rotary motor drive;
    whereby said needle is adapted for both manual insertion and motor-assisted insertion.

21. A biopsy needle as claimed in claim 20 wherein an outer surface of said sampling tube is in contact with the sampled tissue and wherein said motor drive rotates at least said outer surface.

22. A biopsy needle as claimed in claim 20 further comprising a stop, said stop comprising an enlargement of said sampling tube to inhibit over-insertion of said sampling tube into the sampled tissue.

23. A biopsy needle as claimed in claim 22, wherein said enlargement is disposed at a fixed distance from a tip of said sampling tube.

24. A biopsy needle as claimed in claim 22, wherein at least a portion of said stop is integrally formed with at least a portion of said handle.

25. A biopsy needle as claimed in claim 20, wherein said coupling member is separable from said needle and comprises a shaft adapted to be received by said sampling tube, a connecting portion for connecting said motor drive, and a drive portion to engage with said handle.

26. A biopsy needle assembly comprising:
    a single elongated tubular cannula, having an axially extending lumen therethrough and having distal and proximal ends,
    a cannula handle attached to the proximal end of said cannula, said cannula handle extending transversely to the axis of said cannula and having a cavity aligned with and open to the proximal end of said cannula, a distal end of said cannula which is beveled and sharpened and in free fluid communication with the proximal end, a recess or recesses on the outer surface of the said cannula distal end, an expansion on the outer surface of the said cannula distal end, an orifice in said cannula handle in fluid flow communication with said cannula lumen, said orifice being coaxial with said cannula lumen, a stylet having a knob affixed to its proximal end, said knob sized to fit matingly within said orifice, an elongated stylet shaft extending from said knob, slidably received within said cannula lumen, said stylet having a sharpened distal tip which extends distally from the distal end of said cannula, said orifice retaining said knob so that force may be rotatably applied around either axis of direction of said elongated stylet positioned in said orifice without relative rotation between elongated stylet and said elongated cannula, a connector attachment having a knob affixed to its proximal end, said knob being sized to fit matingly within said orifice, said connector attachment having a shaft affixed to its proximal end, said knob and shaft being sized to fit within said orifice of said cannula handle distally and said knob sized to fit an electric drill or electric screw driver proximally, said orifice retaining said knob of said connector attachment so that force maybe rotatably applied around either axis direction of said elongated connector attachment positioned in said orifice without relative rotation between elongated connector attachment and said elongated cannula, an electric drill or electric screw driver, a sheath which is sized to fit around said electric drill or electric screw driver, said sheath having an opening to receive said electric drill or said electric screw driver, said opening having a strap or string to enclose said electric drill or said electric screw driver, a pushrod having a knob affixed to its proximal end, said knob being sized to fit slidably within said orifice, an elongated shaft extending from said pushrod knob, slidably received within said cannula lumen, said pushrod having a blunt distal tip which extends distally from the distal end of said cannula.

27. A biopsy needle as claimed in claim 20 further comprising a motor drive and an insulating, sterile or sterilizable, protective sheath to substantially enclose said motor drive except for a drive shaft, whereby said motor drive may be operated to drive said tissue sampling member while said motor drive is within said sheath.

* * * * *

UNITED STATES PATENT AND TRADEMARK OFFICE
CERTIFICATE OF CORRECTION

PATENT NO. : 6,875,183 B2
DATED : April 5, 2005
INVENTOR(S) : Paul Laurence Cervi It is certified that error appears in the above-identified patent and that said Letters Patent is hereby corrected as shown below:

<u>Title page,</u>
Item [30], Foreign Application Priority Data, please include the following:
-- GB 9926427.7     11/08/1999
    GB 9906257.2     03/19/1999 --.

Signed and Sealed this

Twenty-seventh Day of September, 2005

JON W. DUDAS
*Director of the United States Patent and Trademark Office*